United States Patent
Fu et al.

(10) Patent No.: US 9,315,469 B2
(45) Date of Patent: Apr. 19, 2016

(54) PROCESS FOR DRYING BENDAMUSTINE HYDROCHLORIDE MONOHYDRATE

(71) Applicant: JOHNSON MATTHEY PLC, London (GB)

(72) Inventors: Xing Fu, Acton, MA (US); Jeremy Clinton Wilt, Marlborough, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/206,526

(22) Filed: Mar. 12, 2014

(65) Prior Publication Data

US 2014/0275566 A1 Sep. 18, 2014

Related U.S. Application Data

(60) Provisional application No. 61/782,228, filed on Mar. 14, 2013.

(51) Int. Cl.
*C07D 235/12* (2006.01)
*C07D 235/16* (2006.01)

(52) U.S. Cl.
CPC .................................... *C07D 235/16* (2013.01)

(58) Field of Classification Search
CPC ..................................................... C07D 235/12
USPC ...................................................... 548/309.7
See application file for complete search history.

(56) References Cited

U.S. PATENT DOCUMENTS

| 8,445,524 B2 | 5/2013 | Courvoisier et al. |
| 2013/0184471 A1 | 7/2013 | Schickaneder et al. |
| 2013/0217888 A1 | 8/2013 | Shrawat et al. |
| 2013/0317234 A1 | 11/2013 | Pullagurla et al. |
| 2014/0031560 A1 | 1/2014 | Frey et al. |

FOREIGN PATENT DOCUMENTS

| WO | WO 01/92268 A1 | 12/2001 |
| WO | WO 2010/144675 A1 | 12/2010 |
| WO | WO 2012/059935 A1 | 5/2012 |

OTHER PUBLICATIONS

International Search Report and Written Opinion for Application No. PCT/IB2014/001243, dated Sep. 3, 2014, 8 pp.

Ozegowski et al., gamma-[ I methyl 5 bis-(beta chloraethyl) amino benzimidazoly (2) ] butyric acid hydrochloride, a new cytostatic drug from the series of the Benzimidazole mustards, Zbl. Pharm. 110 (1971) Heft 10, pp. 1013-1020 with English translation.

Gao et al., Synthesis of bendamustine, Chinese Journal of New Drugs, 2007, vol. 16, No. 23, pp. 1960, 1961,1970 with English Abstract.

*Primary Examiner* — Shawquia Jackson

(74) *Attorney, Agent, or Firm* — RatnerPrestia; Shanay M. McCastle

(57) ABSTRACT

Wet bendamustine hydrochloride monohydrate may be dried by a two stage process wherein rapid drying is first carried out to provide a partially dried product, which is then further dried using an inert gas of controlled relative humidity to yield dry bendamustine hydrochloride monohydrate.

18 Claims, 2 Drawing Sheets

BENDAMUSTINE HYDROCHLORIDE MONOHYDRATE

MONOHYDROXY-BENDAMUSTINE

US 9,315,469 B2

PROCESS FOR DRYING BENDAMUSTINE HYDROCHLORIDE MONOHYDRATE

CROSS-REFERENCE TO RELATED APPLICATIONS

This application claims priority to U.S. Provisional Application No. 61/782,228, filed Mar. 14, 2013, the disclosure of which is incorporated herein by reference in its entirety for all purposes.

FIELD OF THE INVENTION

The invention pertains to methods for obtaining dry bendamustine hydrochloride monohydrate in substantially pure form.

BACKGROUND OF THE INVENTION

Bendamustine is a nitrogen mustard used in the treatment of chronic lymphocytic leukemias and lymphomas and is also being studied for the treatment of sarcoma. It belongs to the family of drugs referred to as alkylating agents.

The synthesis of bendamustine hydrochloride monohydrate has been reported by Ozegowski and Krebs, *J. Praktische Chemie*, 4(20), 178-186 (1963) and by Gao et al., *Chinese Journal of New Drugs*, 16(23), 1960-1, 1970 (2007). However, these publications do not specify the purity of the bendamustine hydrochloride monohydrate obtained by the described processes, or the method used for drying of the initially obtained wet product (i.e., bendamustine hydrochloride containing water in addition to the water of crystallization present in the bendamustine hydrochloride monohydrate) to the desired monohydrate form. Bendamustine hydrochloride containing water in various amounts in addition to the water of crystallization present in the monohydrate form of bendamustine hydrochloride is referred to herein as "water-wet" (or simply "wet") or "partially dried."

Published PCT application WO 2010/144675 describes in Example 23, step B, a recrystallization procedure for bendamustine which included the drying of water-wet bendamustine hydrochloride monohydrate after an acetone rinse using a flow of humidified nitrogen (35% to 60% relative humidity). However, this publication does not report the yield of the recrystallized product or the amount of water present in the initial filter cake before drying with the humidified nitrogen. Due to the relatively high solubility of bendamustine hydrochloride monohydrate in mixtures of acetone and water, rinsing of a water-wet filter cake of bendamustine hydrochloride monohydrate with such mixtures can result in a significant yield loss of the product. This loss of product during an acetone wash is clearly detrimental should such a washing step be included as part of a commercial process for producing bendamustine hydrochloride monohydrate. Additionally, bendamustine has been found to be susceptible to hydrolytic degradation upon prolonged exposure to excessive moisture, resulting in the generation of the undesired contaminant monohydroxy-bendamustine (the chemical structures of bendamustine hydrochloride monohydrate and monohydroxy-bendamustine are shown in FIG. 1). However, overdrying of bendamustine hydrochloride monohydrate, resulting in the loss of the desired water of crystallization, can occur if the drying conditions used are too vigorous.

Consequently, there is a need for improved methods for drying water-wet bendamustine hydrochloride monohydrate, whereby high yields of the desired product, which is substantially free of water in excess of the single water of crystallization, are obtained while avoiding overdrying and the formation of degradation by-products.

SUMMARY OF THE INVENTION

The present invention provides methods of obtaining dry bendamustine hydrochloride monohydrate (i.e., bendamustine hydrochloride which contains an approximately 1:1 molar ratio of water to bendamustine hydrochloride, with the water being present as a water of crystallization). In one embodiment, the method comprises the steps of:

a) drying wet bendamustine hydrochloride monohydrate under conditions effective to yield partially dried bendamustine hydrochloride monohydrate having a moisture content of from about 4.4% to about 19% by weight (in one embodiment, a moisture content of about 7% to about 10% by weight); and b) contacting the partially dried bendamustine hydrochloride monohydrate with an inert gas (e.g., nitrogen) of controlled relative humidity (e.g., 0 to about 60% relative humidity) to yield dry bendamustine hydrochloride monohydrate.

In the context of the present invention, "moisture content" (sometimes also referred to herein as "water content") includes free water as well as water of crystallization. Moisture content may be measured by any suitable analytical method, such as Karl Fischer titration.

Step a) may, for example, comprise contacting the wet bendamustine hydrochloride monohydrate with a stream of dry inert gas (e.g., nitrogen, argon) under vacuum.

The present invention has the advantages of being capable of providing the desired monohydrate crystalline form of the API bendamustine hydrochloride in high yield with relatively low levels of impurities arising from hydrolysis of the API (e.g., monohydroxy-bendamustine and/or dihydroxy-bendamustine).

Thus, one aspect of the invention provides dry bendamustine hydrochloride monohydrate, containing less than 0.15% (in another aspect, less than 0.05%) of monohydroxy-bendamustine, as determined by HPLC area %.

Yet other aspects of the invention provide dry bendamustine hydrochloride monohydrate, free or substantially free of any other physical form of bendamustine hydrochloride (such as anhydrous bendamustine hydrochloride).

DETAILED DESCRIPTION OF THE INVENTION

Figure 1:
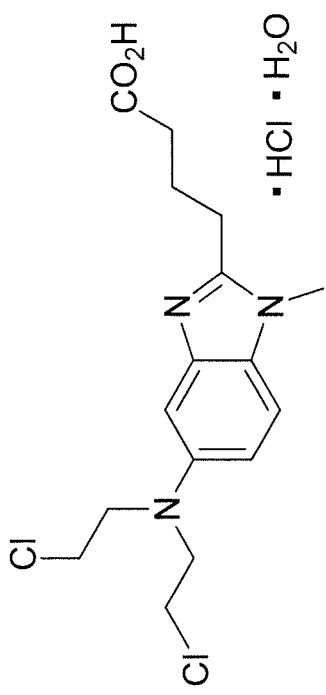
FIG. 1 shows the chemical structures of bendamustine hydrochloride monohydrate and monohydroxy-bendamustine.
Figure 1:
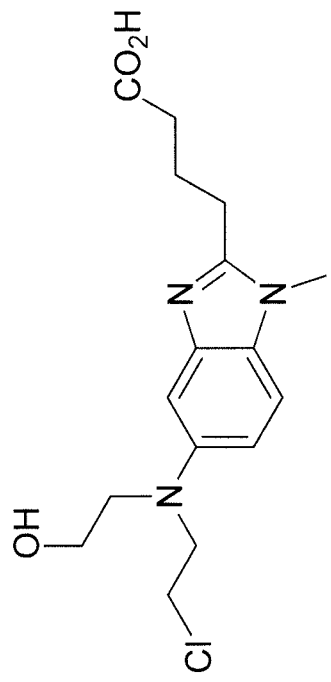

The wet bendamustine hydrochloride monohydrate utilized in the present invention may be obtained using any suitable or known method. In the context of the present invention, the term "wet" is used to mean that the bendamustine hydrochloride monohydrate contains an amount of water in excess of the amount effective to provide the monohydrate of the bendamustine hydrochloride (i.e., an amount of water greater than that needed to attain an about 1:1 molar ratio of water to bendamustine hydrochloride). The wet bendamustine hydrochloride monohydrate may, for example, be in solid, particulate form, with the excess water being present on the surface of and/or within the solid particles of bendamustine hydrochloride monohydrate. The bendamustine hydrochloride monohydrate may be in crystalline form (e.g., in the form of crystals, which may be agglomerated and/or discrete). The wet bendamustine hydrochloride monohydrate may contain, in addition to water, one or more solvents, in particular one or more volatile water-miscible and/or water-immiscible organic solvents such as acetone, t-butyl methyl ether, and the like and mixtures thereof. Typically, the wet bendamustine hydrochloride monohydrate initially contains greater than about 19 weight % water.

In one aspect of the present invention, the wet bendamustine hydrochloride monohydrate is obtained from a crystallization, recrystallization, trituration or precipitation procedure, wherein the wet bendamustine hydrochloride monohydrate is present in solid, particulate form in admixture with a solvent system comprising water in which the bendamustine hydrochloride monohydrate is substantially insoluble and then separated from the bulk of the solvent system by a method such as filtration, decantation, centrifugation or the like to provide the wet bendamustine hydrochloride monohydrate. For example, a relatively crude portion of bendamustine hydrochloride may be recrystallized from a solvent system comprised of water and collected by one of the aforementioned methods to provide a cake (e.g., a filter cake), which may be washed one or more times with additional solvent (which may be the same as, or different from, the solvent system utilized in the recrystallization). In one embodiment of the invention, the filter cake of bendamustine hydrochloride monohydrate is washed with water and then t-butyl methyl ether to provide the wet bendamustine hydrochloride monohydrate. Generally speaking, it will be preferred to avoid the use of acetone in such a washing step, since the solubility of bendamustine hydrochloride monohydrate in acetone or aqueous acetone tends to result in unacceptably high yield losses.

The wet bendamustine hydrochloride monohydrate is subjected to an initial drying step in which the water content is relatively rapidly reduced to a value less about 19% by weight while at the same time avoiding overdrying (wherein the water of crystallization which is needed to form the desired monohydrate is wholly or partially removed). Pure bendamustine hydrochloride monohydrate should theoretically contain about 4.4% by weight water. Consequently, the water content should be monitored (e.g., by Karl Fischer titration) during the initial drying stage so as to ensure that a level of from about 4.4 to about 19 weight percent is attained. Generally speaking, it will be desirable to target attainment of a water content of from about 7 to about 10 weight percent during the initial drying stage.

In one embodiment of the invention, the initial drying step is carried out by contacting the wet bendamustine hydrochloride monohydrate with dry inert gas under vacuum. The dry inert gas may be in the form of a stream. The dry inert gas advantageously may have a relative humidity of not greater than about 10% relative humidity, not greater than about 5% relative humidity, or essentially 0% relative humidity. The dry inert gas may be comprised of nitrogen and/or argon, for example. In one embodiment of the invention, a cake of wet bendamustine hydrochloride monohydrate is present in a filter, wherein the cake is supported on a perforated plate or the like. A vacuum is applied beneath the perforated plate so as to draw dry inert gas introduced above the perforated plate down through the cake. The dry inert gas, as it passes through the cake, helps to volatilize and remove water and solvent present in the cake. By rapidly drying to a moisture content of less than about 19% by weight, it has been discovered that the formation of monohydroxy-bendamustine (or other impurities formed by hydrolysis of bendamustine) may be reduced. In various embodiments of the invention, the dry bendamustine hydrochloride monohydrate obtained contains less than 0.15%, less than 0.10%, or less than 0.05% monohydroxy-bendamustine, as determined on an HPLC area % basis. Typically, drying temperatures of around room temperature (e.g., about 10° C. to about 35° C.) will be suitable. The dry inert gas may, for example, be passed through or over the wet bendamustine hydrochloride monohydrate. A vacuum may be applied to further facilitate drying, with lower pressures (higher vacuum) generally tending to accelerate the rate of drying. Generally speaking, it will be desirable to select conditions such that the target water content of the wet bendamustine hydrochloride monohydrate is achieved rapidly, for example, in less than about 48 hours or less than about 24 hours or even less than about 12 hours, depending upon the size of the batch of wet bendamustine hydrochloride monohydrate being dried.

In one embodiment of the invention, the wet bendamustine hydrochloride monohydrate is dried as a cake on a filter (covered with an appropriately sized polyethylene filter cover) by supplying an inert gas such as argon or nitrogen gas to the top of the filter while applying vacuum at the bottom of the filter for about 1 to about 4 hours at a time before sampling the product and measuring its water content. If the desired water content has not yet been reached, vacuum and the flow of gas are resumed and drying continued for another about 1 to about 4 hours before the water content is again measured. The wet bendamustine hydrochloride monohydrate may be dried until its water content is less than or equal to 19% by weight and greater than or equal to 5.4% by weight, in one embodiment of the invention. Once the desired water content is attained, a humidity generator may be connected to the top of the filter. The partially dried bendamustine hydrochloride monohydrate is subjected to further drying at, for example, about 15° C. to about 30° C. to produce the dry bendamustine hydrochloride monohydrate by mixing the filter cake as an inert gas stream (e.g., a nitrogen and/or argon stream) having 0% to about 60% relative humidity passes over the filter cake.

Alternatively or additionally, one or more other techniques may be used in the first stage drying step to quickly reduce the initial water content of the wet bendamustine hydrochloride monohydrate to within the desired range, yielding the partially dried bendamustine hydrochloride monohydrate. Such techniques include, without limitation, physical and/or chemical methods such as centrifugation, vacuum drying, spray drying, and solvent rinsing, particularly rinsing with water miscible solvents other than acetone in which bendamustine hydrochloride monohydrate has limited solubility.

The partially dried bendamustine hydrochloride monohydrate obtained in the initial drying step is then subjected to a second stage drying step wherein the partially dried bendamustine hydrochloride monohydrate is contacted with an inert gas (e.g., nitrogen, argon) of controlled relative humidity to yield dry bendamustine hydrochloride monohydrate. The inert gas of controlled relative humidity may be provided in the form of a stream, such as a stream which flows over and/or through a portion of the partially dried bendamustine hydrochloride. For example, the portion of partially dried bendamustine hydrochloride may be supported as a cake on a porous support, such as a filter, gas permeable membrane, screen or the like, and a stream of inert gas of controlled relative humidity introduced in a manner effective to cause the inert gas stream to pass through the cake. In another embodiment, a fluid (fluidized) bed drying process may be practiced, wherein particles of the material being dried are suspended in the inert gas of controlled relative humidity. Alternatively, a portion of partially dried bendamustine hydrochloride may be placed in an enclosed chamber and the head space of the enclosed chamber filled with the inert gas of controlled relative humidity. After a period of time, the head space may be flushed with a fresh amount of inert gas of controlled relative humidity (the fresh portion of inert gas may, for example, have a higher RH than the inert gas initially introduced into the head space). This flushing and refilling process may be repeated as many times as may be needed to attain the desired dry bendamustine hydrochloride monohydrate.

In the context of the present invention, "dry" bendamustine hydrochloride monohydrate means bendamustine hydrochloride which contains an approximately 1:1 molar ratio of water to bendamustine hydrochloride. For example, the dry bendamustine hydrochloride monohydrate obtained by the present invention may have a water:bendamustine hydrochloride molar ratio of about 1:1 to about 1.25:1. In certain embodiments, the product obtained is free or substantially free of the anhydrous form of bendamustine hydrochloride. In other embodiments, the product obtained is free or substantially free of any other physical form of bendamustine hydrochloride monohydrate. The relative humidity of the inert gas (which may be supplied in the form of a stream) may be constant throughout the second stage of drying or may be varied as may be desired. Typically, relative humidities of from 0 to about 60% may be utilized. The inert gas may be nitrogen or argon, for example.

As a result of the above-described drying procedure, the dry bendamustine hydrochloride monohydrate obtained will typically be free or substantially free of any organic solvent that may have initially been present in the wet bendamustine hydrochloride monohydrate or partially dried bendamustine hydrochloride monohydrate.

Methods and equipment suitable for providing an inert gas having a desired relative humidity are known in the art and any of such methods and equipment may be adapted for use in the practice of the present invention. For example, on a laboratory scale, a Model RH-200 Relative Humidity Generator available from L&C Science and Technology, Hialeah, Fla., may be utilized. In one embodiment of the invention, a relative humidity generator is used which is capable of supplying a gas having a defined relative humidity value (RH), for example, to a device (e.g., a filter apparatus, an enclosed chamber, a fluidized bed) containing the partially dried bendamustine hydrochloride.

At the beginning of the second drying stage, pure (dry) inert gas (e.g., nitrogen gas, argon gas) may be used. Once the water content has dropped to within the range of from about 5.4% to about 7% by weight, for example, the relative humidity of the inert gas may be increased gradually to 35% or greater and further drying of the partially dried bendamustine hydrochloride monohydrate is continued until the batch meets the specification for dry bendamustine hydrochloride monohydrate (about 4.4% by weight water). During the second stage drying step, the temperature may, for example, suitably be, for example, around room temperature, e.g., about 10° C. to about 35° C. The water content of the bendamustine hydrochloride monohydrate may be monitored during the second drying stage by any suitable method such as Karl Fischer titration. When the desired level of dryness is achieved, contacting of the bendamustine hydrochloride monohydrate with the inert gas of controlled relative humidity is discontinued. The second drying stage is carried out in a way which limits, and in one embodiment avoids, overdrying (wherein the anhydrous form of bendamustine hydrochloride is generated). Typically, the second drying stage takes from about 8 to about 30 hours to complete, depending upon the batch size being dried, the drying conditions and other factors.

EXAMPLES

A 900 gram sample of wet bendamustine hydrochloride monohydrate was dried in a table-top filter with a pure nitrogen stream (0% relatively humidity) under vacuum in an initial drying stage to lower the water content of the sample to within the range of 4.4% to 19% by weight (with a target of 7% to 10% by weight). The wet bendamustine hydrochloride monohydrate had been obtained as a filter cake from a recrystallization procedure, where water and then t-butyl methyl ether had been used to wash the filter cake. The water content was monitored by Karl Fischer (KF) titration testing. Once the water content was found to have dropped to within this range, the vacuum was removed from the system and the relative humidity of the nitrogen stream was adjusted and controlled (within the range of 0% to 60%) to complete the drying procedure, taking care to keep the product in monohydrate form (i.e., overdrying of the product was avoided such that the stoichiometric ratio of water to bendamustine hydrochloride did not fall below about 1:1). This second stage of drying took place over about 24 hours. The dry bendamustine hydrochloride monohydrate product obtained from this drying process was found to contain less than 0.05% (as a % of the total area under the curve of an HPLC trace) of the undesired monohydroxy-bendamustine byproduct. The amount of monohydroxy-bendamustine present may be determined using the following analytical method:

Chromatographic Conditions:
Column: Sunfire C18, 150×4.6 mm, 3.5 μm
Mobile Phase:
    Solvent A: 0.1% Trifluoroacetic acid in water
    Solvent B: 0.05% Trifluoroacetic acid in acetonitrile
Gradient:

| Time (Minutes) | % A | % B |
|---|---|---|
| 0.0 | 95 | 5 |
| 5.0 | 95 | 5 |
| 25.0 | 40 | 60 |
| 27.0 | 0 | 100 |
| 30.0 | 0 | 100 |
| 30.1 | 95 | 5 |
| 37.0 | 95 | 5 |

Detection: UV 235 nm
Sample Diluent: N,N-Dimethylformamide
Injection Volume: 10 μL
Flow Rate: 1.0 mL/min The HPLC area % of a particular component is the percentage represented by the area under the peak for that component of the total area under the curve of an HPLC trace for an analyzed sample.

Figure 2:
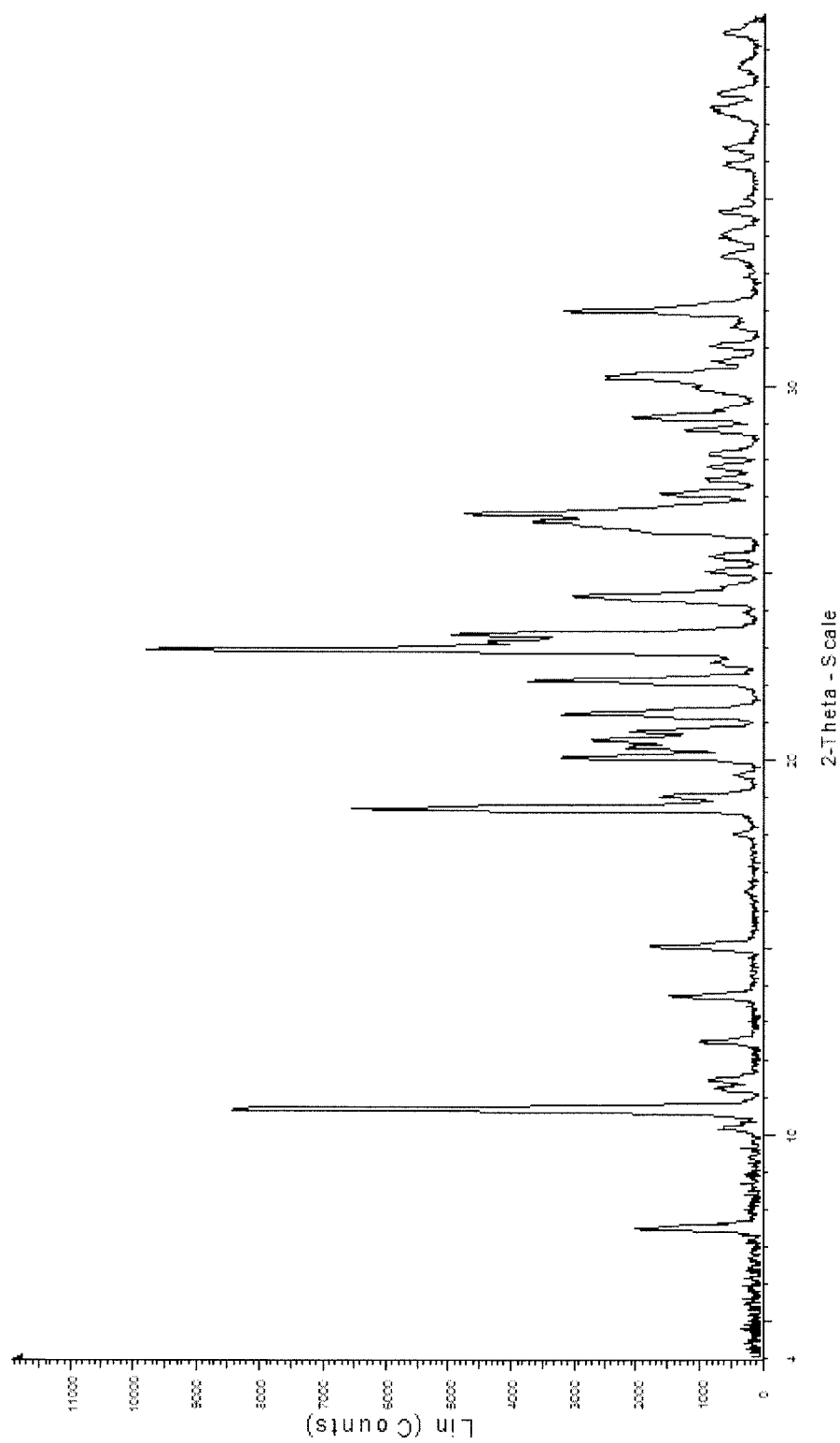
FIG. 2 shows the XRPD pattern of a sample of dry bendamustine hydrochloride monohydrate obtained in accordance with the present invention as described in the Examples.

The x-ray powder diffraction (XRPD) pattern of the dry bendamustine hydrochloride monohydrate product obtained is shown in FIG. 2.

By way of comparison, a similar sample of wet bendamustine hydrochloride monohydrate was dried under a nitrogen stream having approximately 35% relative humidity. The yield of bendamustine hydrochloride monohydrate using this procedure was more than 80%. However, on a 900 g scale, the process required eight to twelve days to reach the desired final water content (i.e., dry bendamustine hydrochloride monohydrate) due to the inefficiency of water removal. During this extended drying period, the bendamustine exhibited a significant amount of degradation into monohydroxy-bendamustine, due to hydrolysis. The level of monohydroxy-bendamustine in the final dry product was increased to 0.2%, as determined by HPLC area %, which is a higher level than recommended by current ICH guidelines.

What is claimed is:

1. A method of obtaining dry bendamustine hydrochloride monohydrate, comprising the steps of:
    a) drying wet bendamustine hydrochloride monohydrate under conditions effective to yield partially dried bendamustine hydrochloride monohydrate having a moisture content of about 4.4% to about 19%; and
    b) contacting the partially dried bendamustine hydrochloride monohydrate with an inert gas of controlled relative humidity to yield dry bendamustine hydrochloride monohydrate.

2. The method of claim 1, wherein step a) comprises contacting the wet bendamustine hydrochloride monohydrate with a stream of dry inert gas under vacuum.

3. The method of claim 1, wherein the inert gas is nitrogen.

4. The method of claim 2, wherein the dry inert gas is nitrogen.

5. The method of claim 1, wherein the inert gas is argon.

6. The method of claim 2, wherein the dry inert gas is argon.

7. The method of claim 1, wherein in step b) the partially dried bendamustine hydrochloride monohydrate is contacted with a stream of inert gas of controlled relative humidity.

8. The method of claim 1, wherein the partially dried bendamustine hydrochloride monohydrate obtained in step a) has a moisture content of from about 7% to about 10%.

9. The method of claim 1, wherein step b) is carried out at atmospheric pressure.

10. The method of claim 1, wherein step a) and step b) are carried out at a temperature within the range of from about 10° C. to about 35° C.

11. The method of claim 1, wherein the inert gas in step b) has a relative humidity of from 0 to about 60%.

12. The method of claim 1, wherein the dry bendamustine hydrochloride monohydrate contains less than 0.15%, as determined by HPLC area %, of monohydroxy-bendamustine.

13. The method of claim 1, wherein the water content of the wet bendamustine hydrochloride monohydrate is measured about every 1 to about 4 hours during step a) until a moisture content within the range of from about 7% to about 10% by weight is achieved.

14. The method of claim 1, wherein the wet bendamustine hydrochloride monohydrate is obtained by a recrystallization procedure involving washing a cake of wet bendamustine hydrochloride monohydrate with water followed by washing the cake with t-butyl methyl ether.

15. The method of claim 1, wherein step a) is completed within about 48 hours.

16. The method of claim 1, wherein step a) is completed within about 24 hours.

17. The method of claim 1, wherein step a) is completed within about 12 hours.

18. The method of claim 1, wherein the relative humidity of the inert gas is varied during step b).

* * * * *